(12) United States Patent
Sawasaka et al.

(10) Patent No.: US 11,692,957 B2
(45) Date of Patent: Jul. 4, 2023

(54) METHOD FOR CALCULATING CONCENTRATION OF DETECTION TARGET GAS

(71) Applicant: Nissha Co., LTD., Kyoto (JP)

(72) Inventors: Shunsuke Sawasaka, Kyoto (JP); Masaya Fukuda, Kyoto (JP); Harumi Kuribayashi, Osaka (JP)

(73) Assignee: NISSHA CO., LTD., Kyoto (JP)

( * ) Notice: Subject to any disclaimer, the term of this patent is extended or adjusted under 35 U.S.C. 154(b) by 9 days.

(21) Appl. No.: 17/616,988

(22) PCT Filed: May 19, 2020

(86) PCT No.: PCT/JP2020/019764
§ 371 (c)(1),
(2) Date: Dec. 6, 2021

(87) PCT Pub. No.: WO2020/246228
PCT Pub. Date: Dec. 10, 2020

(65) Prior Publication Data
US 2022/0170872 A1 Jun. 2, 2022

(30) Foreign Application Priority Data
Jun. 6, 2019 (JP) .................................. 2019-106044

(51) Int. Cl.
*G01N 27/12* (2006.01)
*G01N 33/00* (2006.01)

(52) U.S. Cl.
CPC ........... *G01N 27/12* (2013.01); *G01N 33/007* (2013.01)

(58) Field of Classification Search
CPC ......... G01N 2001/2244; G01N 33/497; G01N 33/4972; G01N 27/16; G01N 27/12; G01N 33/004; G01N 33/0031
See application file for complete search history.

(56) References Cited

U.S. PATENT DOCUMENTS 4,620,437 A * 11/1986 Takami ................ G01N 27/122 338/34
5,061,447 A * 10/1991 Ono ....................... G01N 27/16 324/706

(Continued)

FOREIGN PATENT DOCUMENTS

CN 101241101 A * 8/2008
CN 206020323 U * 3/2017

(Continued)

OTHER PUBLICATIONS

"Search Report of Europe Counterpart Application", dated Jul. 4, 2022, p. 1-p. 5.

*Primary Examiner* — David A. Rogers
(74) *Attorney, Agent, or Firm* — JCIPRNET

(57) ABSTRACT

The method for calculating concentration ratio includes: (a) heating a gas sensor element to a temperature at which both of two gas components introduced in a gas sensor element react, and maintaining the temperature for a predetermined period to measure an electrical resistance value of the gas sensor element; (b) heating the gas sensor element to a temperature at which only any of the two gas components reacts, and maintaining the temperature for a predetermined period to measure an electrical resistance value of the gas sensor element; and (c) calculating a concentration ratio of the two gas components based on a combination of the electrical resistance value in (a) and the electrical resistance value in (b).

2 Claims, 13 Drawing Sheets

(a)

(b)

(56) References Cited

U.S. PATENT DOCUMENTS

| | | | | |
|---|---|---|---|---|
| 5,279,795 A * | 1/1994 | Hughes | | G01N 33/0032 |
| | | | | 436/151 |
| 5,447,054 A * | 9/1995 | Modica | | G01N 27/123 |
| | | | | 73/31.06 |
| 5,705,129 A * | 1/1998 | Takahashi | | G01N 33/0037 |
| | | | | 422/90 |
| 5,922,287 A * | 7/1999 | Kato | | G01N 27/16 |
| | | | | 436/152 |
| 6,488,406 B2 * | 12/2002 | Danley | | G01N 25/4833 |
| | | | | 374/33 |
| 6,561,692 B2 * | 5/2003 | Danley | | G01K 17/00 |
| | | | | 374/33 |
| 6,756,016 B2 * | 6/2004 | Miller | | G01N 27/16 |
| | | | | 73/23.31 |
| 7,041,256 B2 * | 5/2006 | Wang | | G01N 27/16 |
| | | | | 422/98 |
| 7,048,844 B2 * | 5/2006 | Chen | | G01N 27/419 |
| | | | | 204/426 |
| 7,360,396 B2 * | 4/2008 | Shoji | | H01M 8/04492 |
| | | | | 73/25.04 |
| 7,566,848 B2 * | 7/2009 | Takahashi | | G01N 33/005 |
| | | | | 219/202 |
| 8,056,394 B2 * | 11/2011 | Frerichs | | G01N 27/4143 |
| | | | | 73/25.01 |
| 8,265,881 B1 * | 9/2012 | Lakhotia | | G01N 33/0059 |
| | | | | 204/406 |
| 8,425,846 B2 * | 4/2013 | Takahashi | | G01N 27/16 |
| | | | | 422/98 |
| 9,823,211 B1 * | 11/2017 | Allen | | G01N 33/0031 |
| 10,338,021 B2 * | 7/2019 | Graunke | | G01N 33/0016 |
| 10,578,573 B2 * | 3/2020 | Zanella, Sr. | | G01N 27/16 |
| 10,948,469 B2 * | 3/2021 | Zanella, Sr. | | G01N 27/16 |
| 11,156,577 B2 * | 10/2021 | Graunke | | G01N 27/128 |
| 11,199,515 B2 * | 12/2021 | Ura | | G01N 33/0009 |
| 11,399,737 B2 * | 8/2022 | Ratto | | A61B 5/082 |
| 11,448,539 B2 * | 9/2022 | Losio | | G01F 1/698 |
| 11,543,396 B2 * | 1/2023 | Swanson | | G01N 33/0016 |
| 2006/0060788 A1 * | 3/2006 | Uchida | | G01J 5/12 |
| | | | | 250/343 |
| 2016/0313288 A1 * | 10/2016 | Theuss | | G01N 29/2425 |
| 2019/0025233 A1 * | 1/2019 | Tanaka | | G01N 25/30 |
| 2019/0041353 A1 * | 2/2019 | Matsukura | | G01N 27/4071 |
| 2020/0025701 A1 * | 1/2020 | Brown | | G01N 27/16 |

FOREIGN PATENT DOCUMENTS

| | | | | |
|---|---|---|---|---|
| DE | 10008969 C2 * | 10/2002 | | G01N 27/12 |
| JP | H08-285803 | 11/1996 | | |
| JP | H11160266 A * | 6/1999 | | |
| JP | 2000-221153 | 8/2000 | | |
| JP | 2001124716 A * | 5/2001 | | |
| JP | 2016211896 A * | 12/2016 | | |
| JP | 2018169278 A * | 11/2018 | | |
| RU | 2206082 C1 * | 6/2003 | | G01N 27/12 |

* cited by examiner

METHOD FOR CALCULATING CONCENTRATION OF DETECTION TARGET GAS

CROSS REFERENCES TO RELATED APPLICATIONS

This application is a continuation of International Application No. PCT/JP2020/019764, filed on May 19, 2020, which claims priority to Japanese Patent Application 2019-106044, filed on Jun. 6, 2019, which is incorporated herein by reference.

TECHNICAL FIELD

The present disclosure relates to a method for calculating a concentration ratio of a two component gas and a method for calculating a concentration of a detection target gas.

BACKGROUND

A method that introduces a test gas containing two gas components and a detection target gas in a gas sensor element and calculates a concentration of the detection target gas has been known (for example, see Patent Document 1). This method uses a gas sensor element 100 highly sensitive to alcohol and a reference sensor element 200 whose properties other than sensitivity to alcohol are the same as those of the gas sensor element (see FIG. 13). A test gas containing two gas components and alcohol is introduced in the gas sensor element 100. Concurrently with this, two gas components are introduced in the reference sensor element 200 via alcohol removing means 210. In the gas sensor element 100, a resistance value changes due to the introduced alcohol, but because no alcohol is introduced in the reference sensor element 200, a resistance value does not change in the reference sensor element 200. By detecting a difference in the resistance values between the gas sensor element and the reference sensor element, an alcohol concentration in the test gas can be detected.

CITATION LIST

Patent Literature

Patent Document 1: JP 8-285803 A

SUMMARY

Problems to be Solved by the Present Disclosure

However, the alcohol concentration detected by the conventional method is a concentration containing the two gas components, and therefore there has been a problem that the concentration of the detection target gas cannot be accurately obtained. In addition, there has been a problem in the reference sensor element in that it is difficult to find what proportion each of the two gas components is contained.

In order to solve the problems described above, an object of the present disclosure is to provide a calculation method that can highly accurately obtain a concentration of a detection target gas using two gas sensor elements. Further, an object of the present disclosure is to provide a method for calculating a concentration ratio of a two component gas that can obtain a concentration ratio of two gas components using one gas sensor element.

Features for Solving the Problems

Some aspects will be described below as means to solve the problems. These aspects can be combined optionally, as needed.

A method for calculating concentration ratio of two component gas according to the present disclosure includes: (a) heating a gas sensor element to a temperature at which both of two gas components introduced in a gas sensor element react, and maintaining the temperature for a predetermined period to measure an electrical resistance value of the gas sensor element; (b) heating the gas sensor element to a temperature at which only any of the two gas components reacts, and maintaining the temperature for a predetermined period to measure an electrical resistance value of the gas sensor element; and (c) calculating a concentration ratio of the two gas components based on a combination of the electrical resistance value in (a) and the electrical resistance value in (b).

The two gas components may be hydrogen and carbon monoxide.

A method for calculating concentration of detection target gas according to the present disclosure includes: (a) introducing a detected gas containing two gas components and one detection target gas in a gas sensor element and calculating an interim concentration of the detection target gas; (b) introducing the two gas components in a reference sensor element having a same property as a property of the gas sensor element, heating the reference sensor element to a temperature at which both of the two gas components react, and maintaining the temperature for a predetermined period to measure an electrical resistance value of the reference sensor element concurrently with (a); (c) heating the reference sensor element to a temperature at which only any of the two gas components reacts, and maintaining the temperature for a predetermined period to measure an electrical resistance value of the reference sensor element; (d) calculating a concentration ratio of the two gas components based on a combination of the electrical resistance value in (b) and the electrical resistance value in (c); (e) correcting a calibration curve of the two gas components in the gas sensor element and a calibration curve of the two gas components in the reference sensor element preliminarily prepared based on the concentration ratio; (f) using the calibration curve in the reference sensor element corrected in (e) to calculate a concentration of the two gas components at the electrical resistance value in (b); (g) using the calibration curve in the gas sensor element corrected in (e) to convert the concentration of the two gas components calculated in (f) into a concentration of the detection target gas; and (h) calculating a difference between the interim concentration of the detection target gas calculated in (a) and the concentration of the detection target gas converted in (g).

The test gas may be an exhaled gas. The two gas components may be hydrogen and carbon monoxide. The detection target gas may be ethanol.

Advantageous Effects of Disclosure

The method for calculating concentration ratio of two component gas according to the present disclosure is configured to include: (a) heating the gas sensor element to the temperature at which both of the two gas components introduced in the gas sensor element react and maintaining the temperature for the predetermined period to measure the electrical resistance value of the gas sensor element; (b) heating the gas sensor element to the temperature at which only any of the two gas components reacts, maintaining the temperature for the predetermined period to measure the electrical resistance value of the gas sensor element; and (c) calculating a concentration ratio of the two gas components based on the combination of the electrical resistance value in (a) and the electrical resistance value in (b).

Therefore, with the method of the present disclosure, the use of one gas sensor element allows obtaining the concentration ratio of the two gas components.

The method for calculating concentration of detection target gas according to the present disclosure is configured to include: (a) introducing the detected gas containing the two gas components and one detection target gas in the gas sensor element and calculating the interim concentration of the detection target gas; (b) introducing the two gas components in the reference sensor element having the same property as the property of the gas sensor element, heating the reference sensor element to the temperature at which both of the two gas components react, and maintaining the temperature for the predetermined period to measure the electrical resistance value of the reference sensor element concurrently with (a); (c) heating the reference sensor element to the temperature at which only any of the two gas components reacts and maintaining the temperature for the predetermined period to measure the electrical resistance value of the reference sensor element; (d) calculating the concentration ratio of the two gas components based on the combination of the electrical resistance value in (b) and the electrical resistance value in (c); (e) correcting the calibration curve of the two gas components in the gas sensor element and the calibration curve of the two gas components in the reference sensor element preliminarily prepared based on the concentration ratio; (f) using the calibration curve in the reference sensor element corrected in (e) to calculate the concentration of the two gas components at the electrical resistance value in (b); (g) using the calibration curve in the gas sensor element corrected in (e) to convert the concentration of the two gas components calculated in (f) into the concentration of the detection target gas; and (h) calculating the difference between the interim concentration of the detection target gas calculated in (a) and the concentration of the detection target gas converted in (g).

Therefore, with the methods of the present disclosure, the concentration of the detection target gas can be highly accurately obtained using the two gas sensor elements.

BRIEF DESCRIPTION OF DRAWINGS

FIG. 1(*b*) is a flowchart depicting a method for calculating a concentration ratio of a two component gas.

FIG. 5(*b*) is a schematic cross-sectional view illustrating an example of a reference sensor device using a reference sensor element.

DETAILED DESCRIPTION

Hereinafter, an example of embodiments of a method for calculating a concentration ratio of a two component gas of the present disclosure will be described with reference to the drawings.

Figure 1:
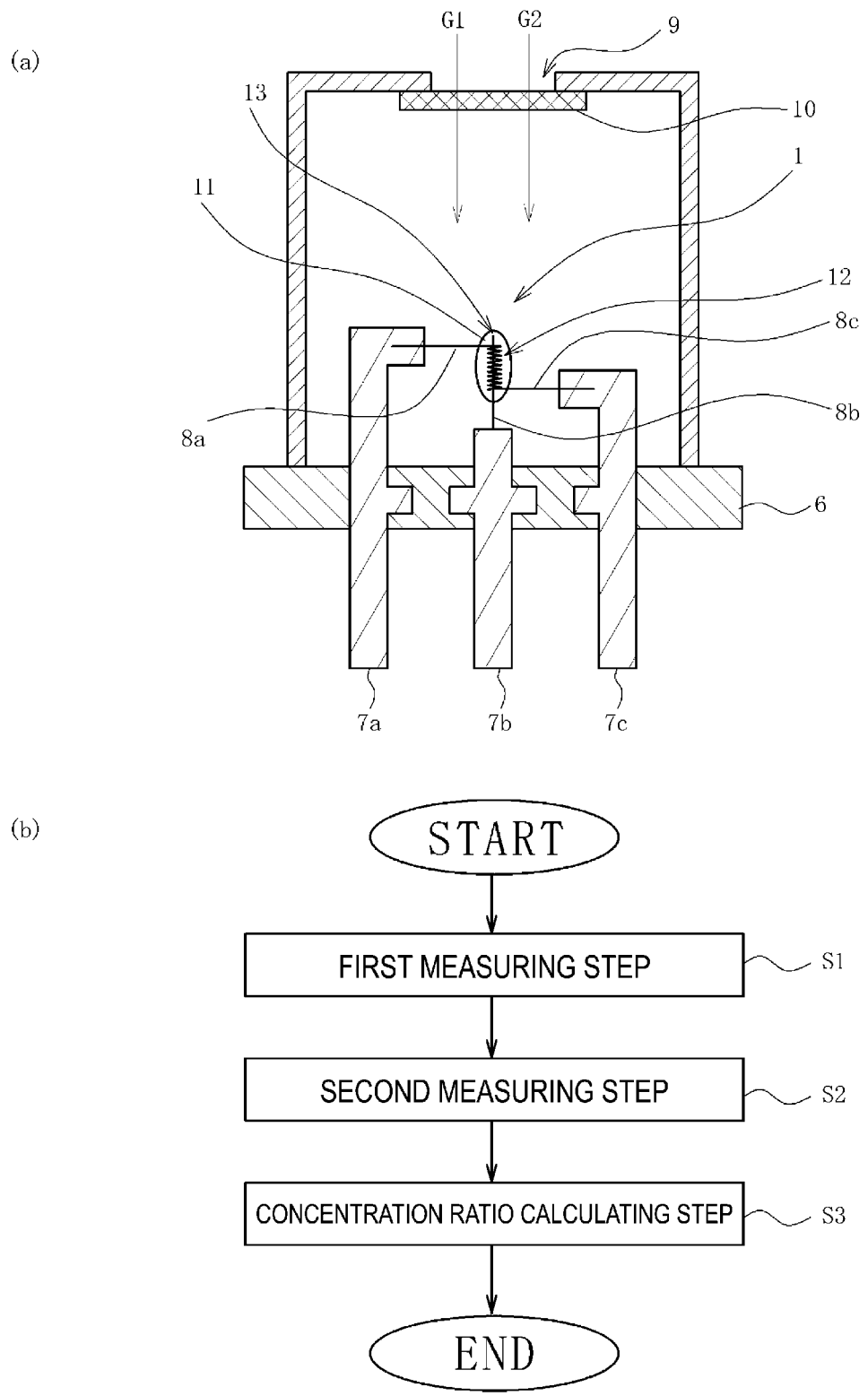
FIG. 1(*a*) is a schematic cross-sectional view illustrating an example of a gas sensor device using a gas sensor element.

The method for calculating the concentration ratio of the two component gas includes: a first measuring step S1 that heats a gas sensor element 1 to a temperature at which both of two gas components G1 and G2 introduced in the gas sensor element 1 react and maintains the temperature for a predetermined period to measure an electrical resistance value of the gas sensor element 1; a second measuring step S2 that heats the gas sensor element 1 to a temperature at which only any of the two gas components G1 and G2 reacts, maintains the temperature for a predetermined period to measure an electrical resistance value of the gas sensor element 1; and a concentration ratio calculating step that calculates concentration ratio of the two gas components G1 and G2 based on a combination of the electrical resistance value in the first measuring step S1 and the electrical resistance value in the second measuring step (see FIG. 1).

The gas sensor element 1 that includes, for example, a gas sensitive body 11, a combined heater-electrode 12, a linear electrode 13, lead wires 8*a* and 8*c*, and a lead wire 8*b* can be used. The gas sensitive body 11 contains a metal oxide semiconductor. The combined heater-electrode 12 has a coil shape and is embedded into the gas sensitive body. The linear electrode 13 passes through the interior of the combined heater-electrode. The lead wires 8*a* and 8*c* extend from both ends of the combined heater-electrode 12 and heat the combined heater-electrode. The lead wire 8*b* extends outside the gas sensitive body from an end portion of the linear electrode 13 (see FIG. 1(*a*)).

As examples of the metal oxide semiconductor contained in the gas sensitive body 11, tin oxide, tungsten oxide, indium oxide, zinc oxide, titanium oxide, strontium titanate, barium titanate, and barium stannate can be used. The gas sensitive body 11 may further contain an additive, such as an appropriate inorganic insulator and catalyst. The inorganic insulator can contain at least one kind selected from alumina and silica, for example. The catalyst can contain at least one kind selected from ruthenium, palladium, antimony, lanthanum, cerium, and molybdenum, for example.

The shape of the gas sensitive body 11 is not particularly limited, and is formed into a spherical shape, such as an ellipsoid shape and a globe shape, as illustrated in FIG. 1, for example. The dimensions of the gas sensitive body 11 are appropriately set, but preferably the diameter of the gas sensitive body 11 is in the range of 0.2 to 0.7 mm. For example, the gas sensitive body 11 is formed into a long ellipsoid shape having a long diameter of 0.5 mm and a short diameter of 0.3 mm.

Three terminals 7a, 7b, and 7c are connected to the three lead wires 8a, 8b, and 8c of the gas sensor element 1, respectively, and a base 6 and a cover 5 that houses the gas sensor element 1 are provided, thus ensuring configuring a gas sensor device. A gas introduction hole 9 is opened in the center of the distal end surface (the ceiling surface) of the cover 5 so that a gas can be introduced in the gas sensor element 1. In addition, the gas introduction holes 9 can be provided with a wire mesh 10 for removing, for example, foreign substances in a test gas.

Both of the two gas components G1 and G2 introduced in the gas sensor element 1 react in the first measuring step, and only one of the gas components reacts in the second measuring step. When it is found what sort of temperature properties the two gas components G1 and G2 have, gas components that can exhibit such reactions can be selected. As an example, the following gives a description using hydrogen and carbon monoxide as the two gas components.

In the first measuring step S1, the gas sensor element 1 is heated to a temperature at which the hydrogen and the carbon monoxide react, and the temperature is maintained for a predetermined period to measure the electrical resistance value of the gas sensor element 1 (see FIG. 1(b)). The temperature at which the hydrogen and the carbon monoxide react can be, for example, from 100° C. to 200° C. in consideration of the temperature properties of these gas components. The predetermined period for maintaining this temperature can be, for example, five seconds or more during which the sensor resistance value can be stably measured. The above-described temperature is maintained for the period described above, and the electrical resistance value of the gas sensor element 1 is measured. The electrical resistance value at this time is configured to be stored in a storage unit, such as a microcomputer, connected to the gas sensor device.

In the second measuring step S2, the gas sensor element 1 is heated to a temperature at which only the hydrogen reacts, and the temperature is maintained for a predetermined period to measure the electrical resistance value of the gas sensor element 1. The temperature at which only the hydrogen reacts can be, for example, from 200° C. to 300° C., in consideration of the temperature property of the hydrogen. The predetermined period for maintaining this temperature can be, for example, from two seconds to five seconds. The above-described temperature is maintained for the period described above, and the electrical resistance value of the gas sensor element 1 is measured. The electrical resistance value at this time is configured to be stored in a storage unit, such as a microcomputer, connected to the gas sensor device.

In the concentration ratio calculating step S3, the concentration ratio of the hydrogen and the carbon monoxide is calculated based on the combination of the electrical resistance value in the first measuring step and the electrical resistance value in the second measuring step. In calculating the concentration ratio, for example, respective calibration curves of the hydrogen and the carbon monoxide preliminarily stored in the storage unit, such as a microcomputer, can be used (see FIG. 2). The calibration curves can be obtained as follows. Electrical resistance values of three kinds of gases (hydrogen 100% gases) that contain only hydrogen and have a low concentration, a medium concentration, and a high concentration are measured at the temperature and the period of the first measuring step, and then the electrical resistance values are measured at the temperature and the period of the second measuring step. Taking the electrical resistance value at the first measuring step on the horizontal axis and taking the electrical resistance value at the second measuring step on the vertical axis, the measured three sets of the electrical resistance values are plotted, thus obtaining the calibration curve of the hydrogen 100% gases. Similarly, electrical resistance values of three kinds of gases (carbon monoxide 100% gases) that contain only carbon monoxide and have a low concentration, a medium concentration, and a high concentration are measured at the temperature and the period of the first measuring step, and then the electrical resistance values are measured at the temperature and the period of the second measuring step. The three sets of the measured electrical resistance values are plotted to obtain calibration curve of the carbon monoxide 100% gases.

Figure 3:
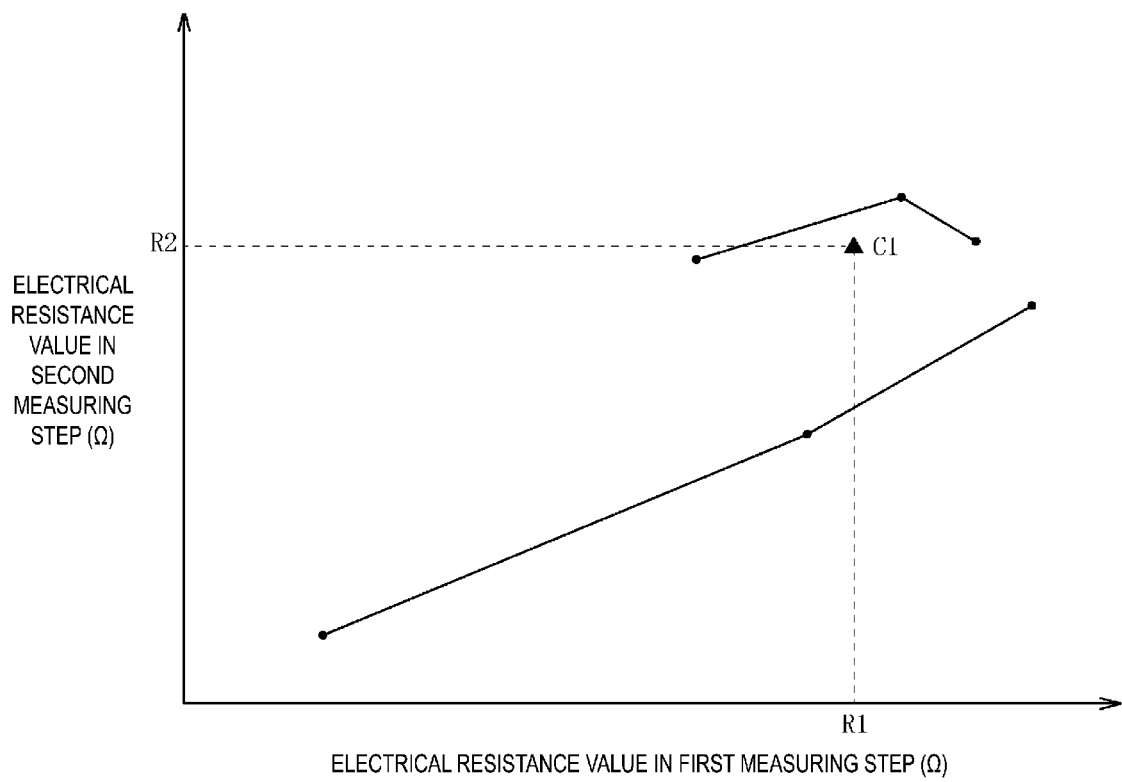
FIG. 3 is a diagram that applies an actually measured value to the calibration curve used in the method for calculating the concentration ratio of the two component gas.
Figure 4:
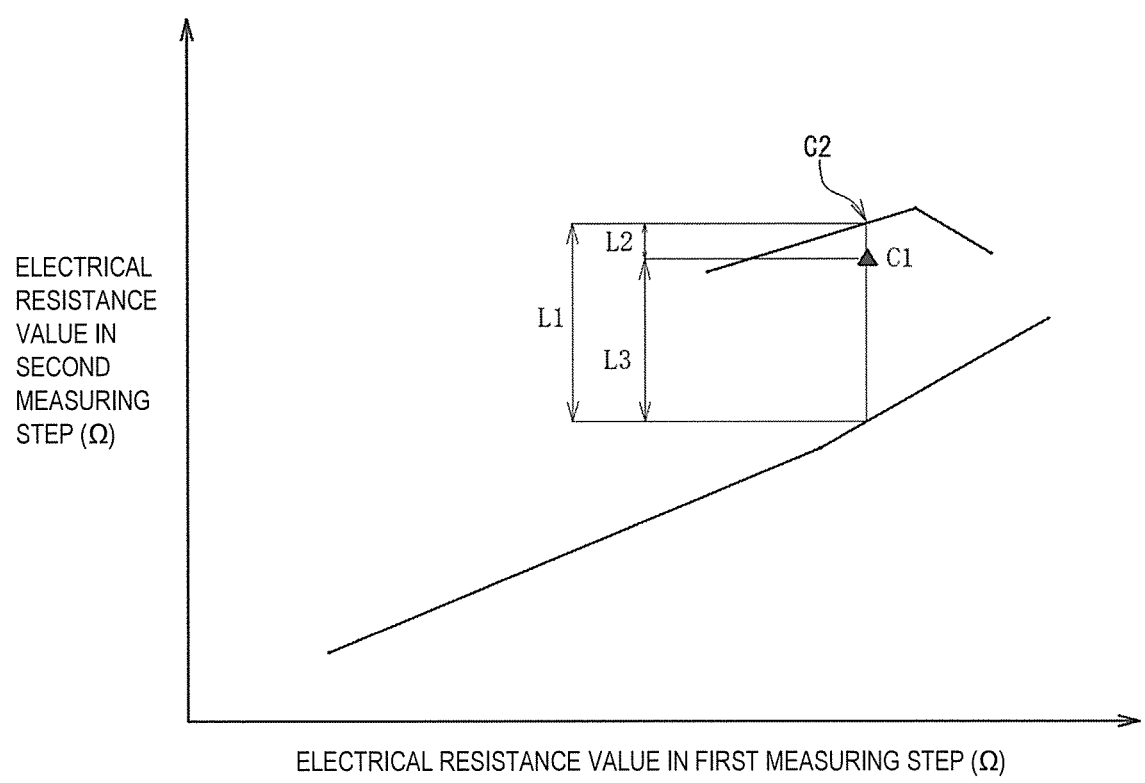
FIG. 4 is a diagram illustrating the method for calculating the concentration ratio of the two component gas from the calibration curve used in the method for calculating the concentration ratio of the two component gas.

A gas of a mixture of hydrogen and carbon monoxide is actually measured, and the two electrical resistance values are applied to the calibration curves described above (see FIG. 3). The drawing illustrates cases where the electrical resistance value in the first measuring step is R1 ($\Omega$) and the electrical resistance value in the second measuring step is R2 ($\Omega$). Assume that an intersection point between R1 and R2 is C1, since C1 is closer to the calibration curve of the carbon monoxide 100% gas than the calibration curve of the hydrogen 100% gas, it can be seen that the carbon monoxide is contained more than the hydrogen. The method for calculating concentration ratio of the hydrogen and the carbon monoxide is as follows. First, as illustrated in FIG. 4, a provisional straight line passing through the intersection point C1 and connecting both calibration curves is drawn, and the length thereof is denoted as L1. Next, a length from an intersection point C2 between the provisional straight line and the calibration curve of the carbon monoxide 100% gas to the intersection point C1 is denoted as L2. The value obtained by (L2×100)/L1 is a ratio of the hydrogen. Assuming that the length from the intersection point C1 to the calibration curve of the hydrogen 100% gas on the provisional straight line is denoted as L3, the value obtained by (L3×100)/L1 is the ratio of the carbon monoxide. The ratio obtained in this way is the concentration ratio of the hydrogen and the carbon monoxide. For example, when L2=0.12 and L3=0.88 are met, the hydrogen concentration is 12% and the carbon monoxide concentration is 88%.

As described above, the concentration ratio of the two gas components introduced in the gas sensor element can be obtained. That is, not only the presence of the two gas components, but also the two gas components are mixed at which ratio can be known.

In the test gas containing the three or more gas components G1, G2, and G3, the two gas components G1 and G2 can be introduced in the gas sensor element, and the concentration ratio thereof can be calculated. In other words, when means for removing the gas component G3 is provided in the gas sensor device, the concentration ratio of the two gas components G1 and G2 can be calculated using one gas sensor element. Examples of the means for removing the gas component G3 include a filter and an adsorbent.

Note that in the method for calculating the concentration ratio of the present disclosure, in addition to hydrogen and carbon monoxide, the following gas components can be used as the combination of the two gas components. For example, two components selected from the group consisting of hydrogen, carbon monoxide, acetone, methane, propane, sulfur dioxide, and a volatile organic compound (VOC) can be used. Note that the temperature and time can be controlled to some extent depending on a composition and a proportion of a material of a semiconductor gas sensor (a gas sensitive body). Therefore, as the combination of the two gas components used in the method for calculating the concentration ratio of the present disclosure, a combustible gas that can be detected by the semiconductor gas sensor can be a candidate for the target.

Next, an example of embodiments of the method for calculating the concentration of the detection target gas of the present disclosure will be described with reference to the drawings.

Figure 5:
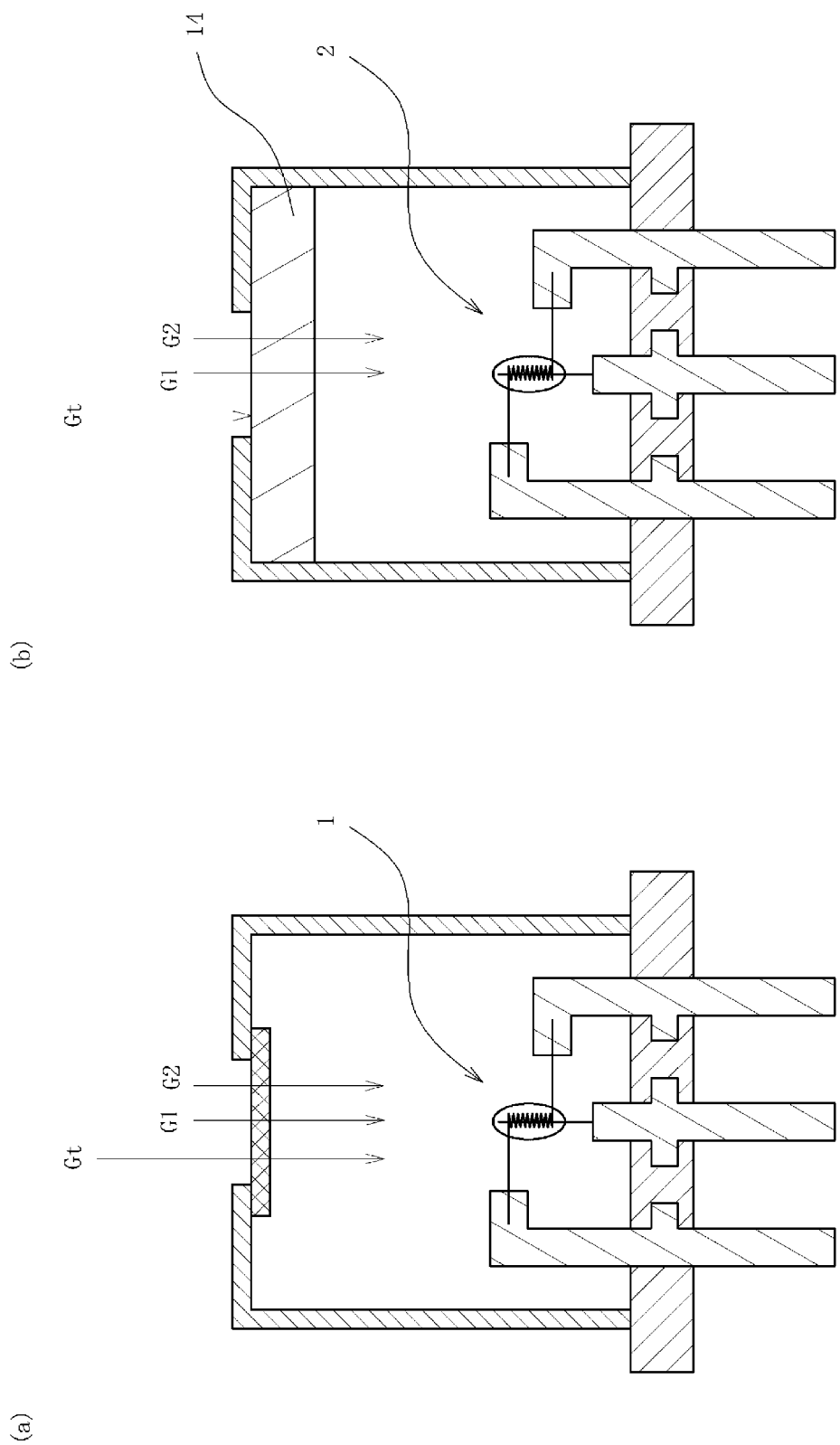
FIG. 5(*a*) is a schematic cross-sectional view illustrating an example of the gas sensor device using the gas sensor element.
Figure 6:
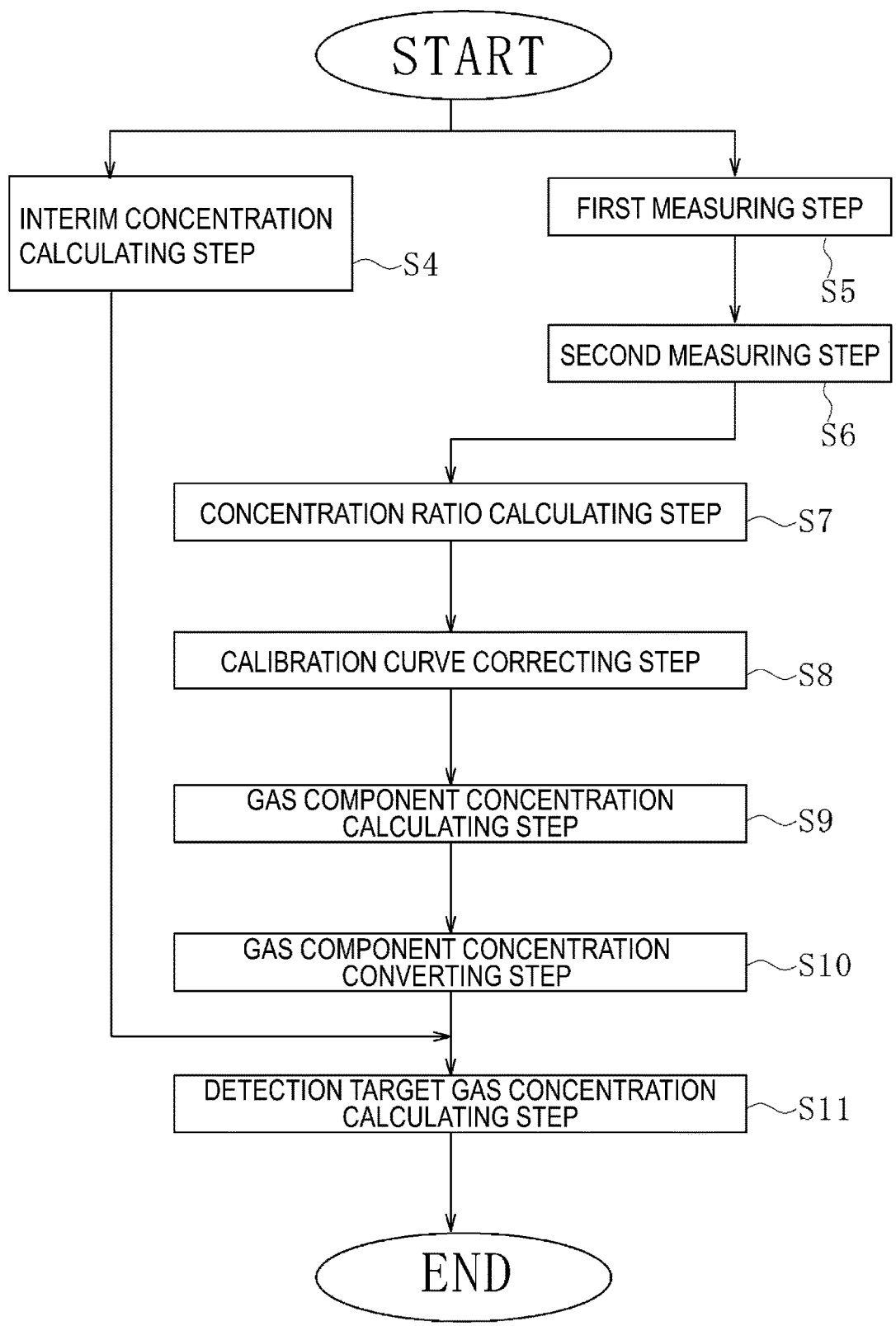
FIG. 6 is a flowchart depicting a method for calculating a concentration of a detection target gas.

The method for calculating the concentration of the detection target gas includes: an interim concentration calculating step S4 that introduces a detected gas containing the two gas components G1 and G2 and one detection target gas Gt in the gas sensor element 1 and calculates an interim concentration of the detection target gas Gt; a first measuring step S5 that introduces the two gas components G1 and G2 in a reference sensor element 2 having the same property as the property of the gas sensor element, heats the reference sensor element 2 to a temperature at which both of the two gas components G1 and G2 react, and maintains the temperature for a predetermined period to measure an electrical resistance value of the reference sensor element 2 concurrently with the interim concentration calculating step S4; a second measuring step S6 that heats the reference sensor element 2 to a temperature at which only any of the two gas components G1 and G2 reacts, maintains the temperature for a predetermined period, and measures an electrical resistance value of the reference sensor element 2; a concentration ratio calculating step S7 that calculates a concentration ratio of the two gas components G1 and G2 based on a combination of the electrical resistance value in the first measuring step S5 and the electrical resistance value in the second measuring step S6; a calibration curve correcting step S8 that corrects the calibration curve 3 of the two gas components G1 and G2 in the gas sensor element 1 and calibration curve 4 of the two gas components G1 and G2 in the reference sensor element 2 preliminarily prepared based on the concentration ratio; a gas component concentration calculating step S9 that uses calibration curve 4' in the reference sensor element corrected in the calibration curve correcting step S8 to calculate concentration of the two gas components G1 and G2 at the electrical resistance value in the first measuring step S5; a gas component concentration converting step S10 that uses calibration curve 3' in the gas sensor element corrected in the calibration curve correcting step S8 to convert the concentration of the two gas components G1 and G2 calculated in the gas sensor element calculating step S9 into a concentration of the detection target gas Gt; and a target gas concentration calculating step S11 that calculates a difference between the interim concentration of the detection target gas Gt calculated in the interim concentration calculating step S4 and the concentration of the detection target gas Gt converted in the gas component concentration converting step S10 (see FIG. 5 and FIG. 6).

In the interim concentration calculating step S4, the test gas containing the two gas components G1 and G2 and one detection target gas Gt is introduced in the gas sensor element 1, and the interim concentration of the detection target gas Gt is calculated (see FIG. 5($a$)). The gas sensor element 1 same as the gas sensor element 1 that has already been described with reference to FIG. 1($a$) is used. The test gas introduced in the gas sensor element 1 contains the two gas components G1 and G2 and the detection target gas Gt. Both of the two gas components G1 and G2 in the reference sensor element 2 react in the first measuring step, and only one of the gas components reacts in the second measuring step. When the two gas components G1 and G2 have what sort of temperature properties are found, gas components that can exhibit such reactions can be selected.

The test gas may be an exhaled gas, the two gas components G1 and G2 may be hydrogen and carbon monoxide, and the detection target gas Gt may be ethanol. That is, the present disclosure can be applied to an exhaled gas analysis device. By exhaling an exhaled gas into an exhaled gas analysis device by an user, the exhaled gas analysis device calculates an ethanol concentration in the exhaled gas. Hereinafter, the description will be given with G1 as hydrogen, G2 as carbon monoxide, and Gt as ethanol.

In the interim concentration calculating step S4, the interim concentration of the ethanol, which is the detection target gas Gt, is calculated. At this time, the interim concentration is calculated using the calibration curve 3 preliminarily stored in the storage unit, such as a microcomputer (see FIG. 7). The calibration curve 3 can be obtained by, for example, as follows. First, a gas containing only the hydrogen (G1) at a low concentration is introduced in the gas sensor element and reacted, and the electrical resistance value is measured. Next, a gas containing only hydrogen at a medium concentration is introduced in the gas sensor element and reacted, and the electrical resistance value is measured. Next, a gas containing only hydrogen at a high concentration is introduced in the gas sensor element and reacted, and the electrical resistance value is measured. By plotting the obtained three electrical resistance values, a calibration curve of the hydrogen (G1) can be obtained. Similarly, calibration curves of the carbon monoxide (G2) and the ethanol (Gt) can be obtained.

An electrical resistance value Rt measured in the interim concentration calculating step S4 is applied to the preliminarily prepared calibration curve 3 described above (see FIG. 7). Since the gas component whose interim concentration is obtained is the ethanol (Gt), a point where the electrical resistance value becomes Rt in the calibration curve of the ethanol can be calculated as an interim concentration Dt of the ethanol. The interim concentration Dt of the ethanol is a concentration in a state also containing the two component gas (the hydrogen and the carbon monoxide). That is, the interim concentration Dt is not an ethanol concentration that is obtained accurately.

In the first measuring step S5, which is performed concurrently with the interim concentration calculating step S4, hydrogen and carbon monoxide are introduced in the reference sensor element 2 having the same property as that of the gas sensor element 1, the reference sensor element 2 is heated to a temperature at which both of the hydrogen and the carbon monoxide react, and the temperature is maintained for a predetermined period to measure the electrical resistance value of the reference sensor element 2 (see FIG. 5($b$) and FIG. 6). The reference sensor element 2 has the same property as that of the gas sensor element 1. Hydrogen and carbon monoxide are introduced in the reference sensor element 2, but ethanol is not introduced. Thus, to introduce the test gas in the reference sensor element 2, the test gas is introduced via, for example, a filter 14 that adsorbs ethanol.

The temperature at which the hydrogen and the carbon monoxide react can be, for example, from 100° C. to 200° C. in consideration of the temperature properties of these gas components. The predetermined period for maintaining this temperature can be, for example, five seconds or more during which the sensor resistance value can be stably measured. The above-described temperature is maintained for the period described above, and the electrical resistance value of the reference sensor element 2 is measured. The electrical resistance value at this time is configured to be stored in a storage unit, such as a microcomputer.

In the second measuring step S6, the reference sensor element 2 is heated to a temperature at which only the hydrogen reacts, and the temperature is maintained for a predetermined period to measure the electrical resistance value of the reference sensor element 2. The temperature at which only the hydrogen reacts can be, for example, from 200° C. to 300° C., in consideration of the temperature property of the hydrogen. The predetermined period for maintaining this temperature can be, for example, from two seconds to five seconds. The above-described temperature is maintained for the period described above, and the electrical resistance value of the reference sensor element 2 is measured. The electrical resistance value at this time is configured to be stored in a storage unit, such as a microcomputer.

With reference to FIG. 5(b), the second measuring step can be performed on hydrogen and carbon monoxide confined in the reference sensor device by the filter 14. Thus, to perform the second measuring step, the user of the exhaled gas analysis device does not need to additionally exhale exhaled air.

Figure 2:
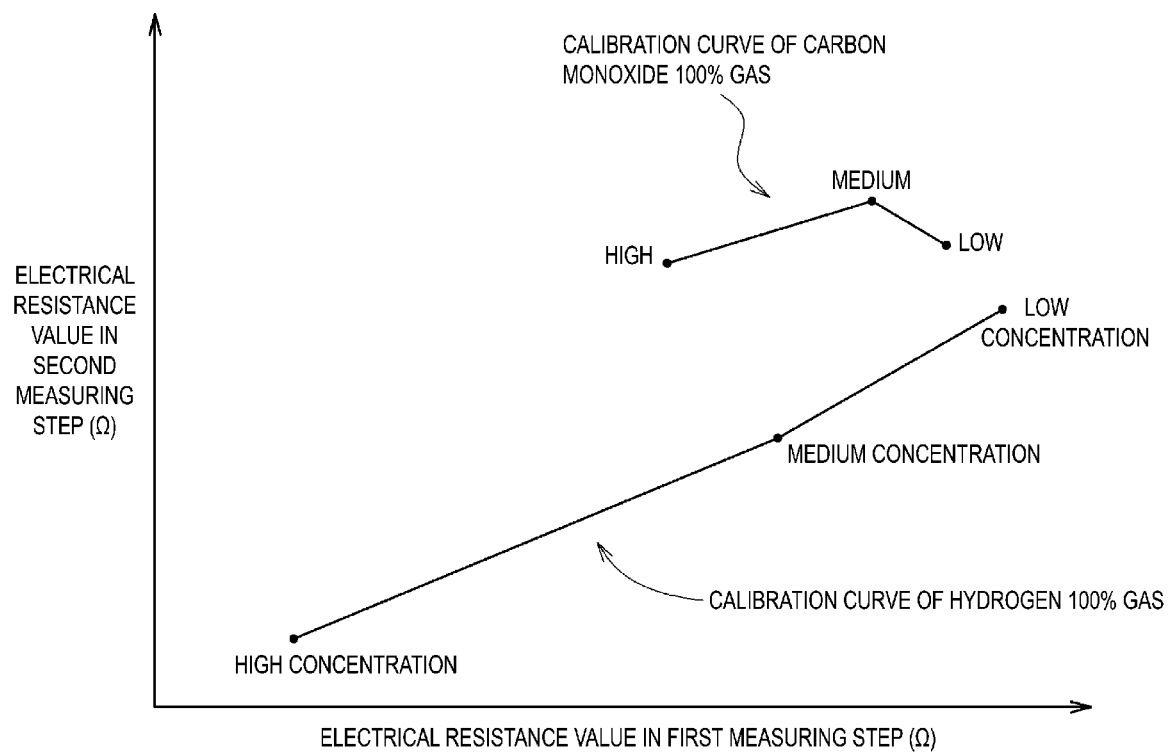
FIG. 2 is an example of a calibration curve used in the method for calculating the concentration ratio of the two component gas.

In the concentration ratio calculating step S7, the concentration ratio of the hydrogen and the carbon monoxide is calculated based on the combination of the electrical resistance value in the first measuring step S5 and the electrical resistance value in the second measuring step S6. As the calculation method, the method having the same content as the already described method with reference to FIG. 2 to FIG. 4 is used.

In a calibration curve correcting step S8, the preliminarily prepared calibration curves are corrected. The calibration curves to be corrected are the following two types. One is the calibration curve 3 of the two gas components (the hydrogen and the carbon monoxide) in the gas sensor element 1, and are the calibration curves used in the interim concentration calculating step S4 (see FIG. 7). The other one is the calibration curve 4 of the two gas components (the hydrogen and the carbon monoxide) in the reference sensor element 2 (see FIG. 8). The ethanol, which is the detection target gas Gt, is removed by the filter 14 and is not introduced in the reference sensor element 2, so reaction with ethanol does not occur. Thus, the electrical resistance value hardly changes, and the calibration curve becomes a lateral linear line. Using the concentration ratio calculated in the concentration ratio calculating step S7, the calibration curves of the two gas components (the hydrogen and the carbon monoxide) in the two kinds of the calibration curves 3 and 4 are corrected by the following equation.

$$f_{Noise} = \alpha \cdot f_{H2} + (1-\alpha) f_{co}$$ [Equation 1]

$\alpha$: Concentration ratio of hydrogen
$f_{H2}$: Calibration curve of hydrogen (G1)
$f_{CO}$: Calibration curve of carbon monoxide (G2)

Figure 9:
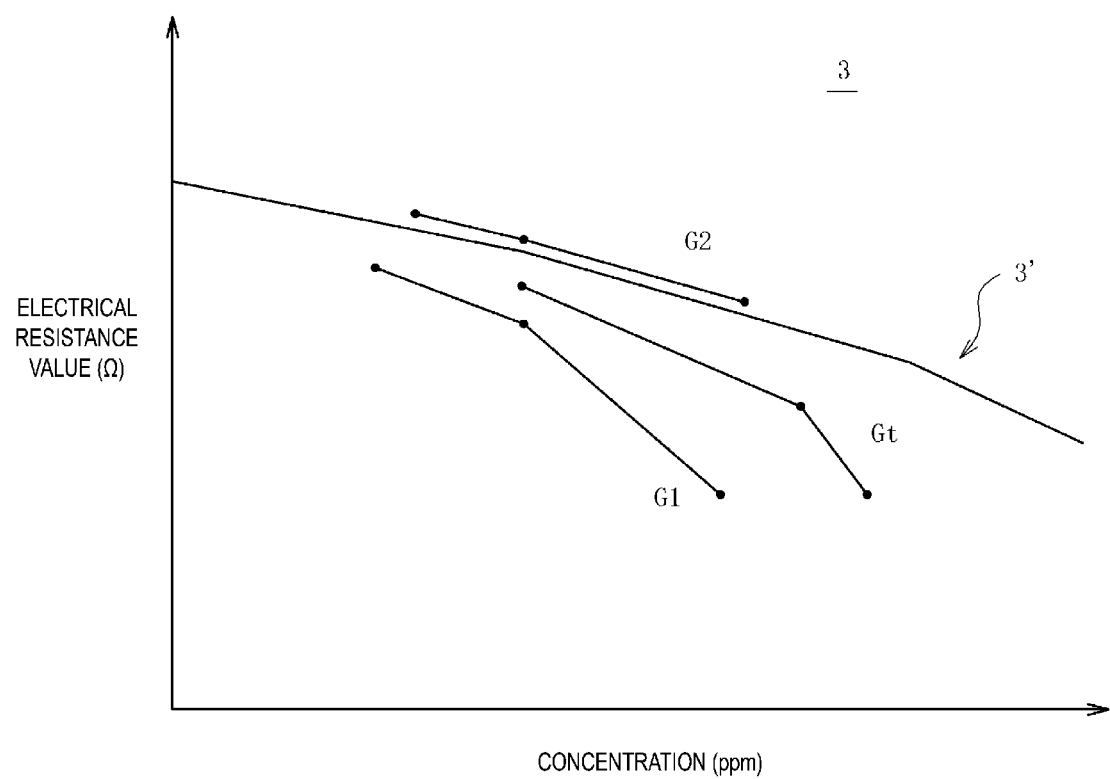
FIG. 9 is a diagram illustrating an example of a calibration curve of the two component gas in the gas sensor element corrected in a calibration curve correcting step.
Figure 10:
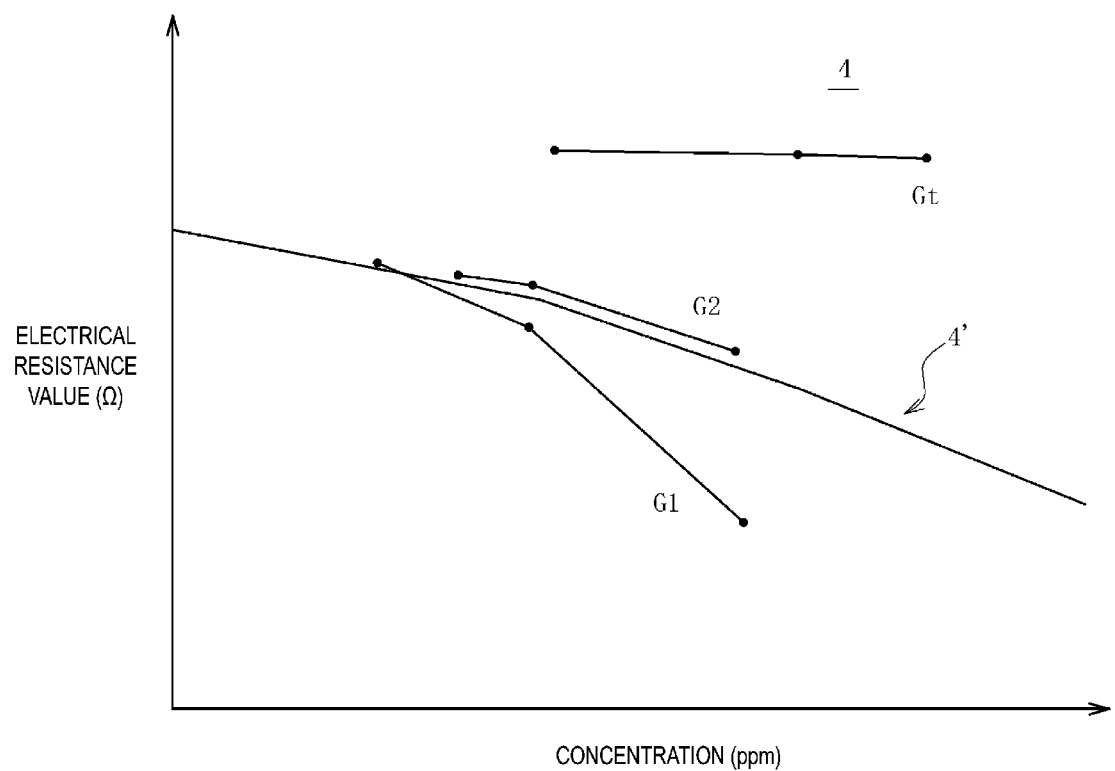
FIG. 10 is a diagram illustrating an example of a calibration curve of the two component gas in the reference sensor element corrected in the calibration curve correcting step.

For example, with the hydrogen of 12%, $\alpha=0.12$, and the calibration curves 3' and 4' after correction become straight lines as in FIG. 9 and FIG. 10, respectively. The calibration curve 3' of the two component gas of the hydrogen and carbon monoxide in the gas sensor element 1 and the calibration curve 4' of the two component gas of the hydrogen and the carbon monoxide in the reference sensor element 2 can be obtained by the calibration curve correcting step.

Figure 11:
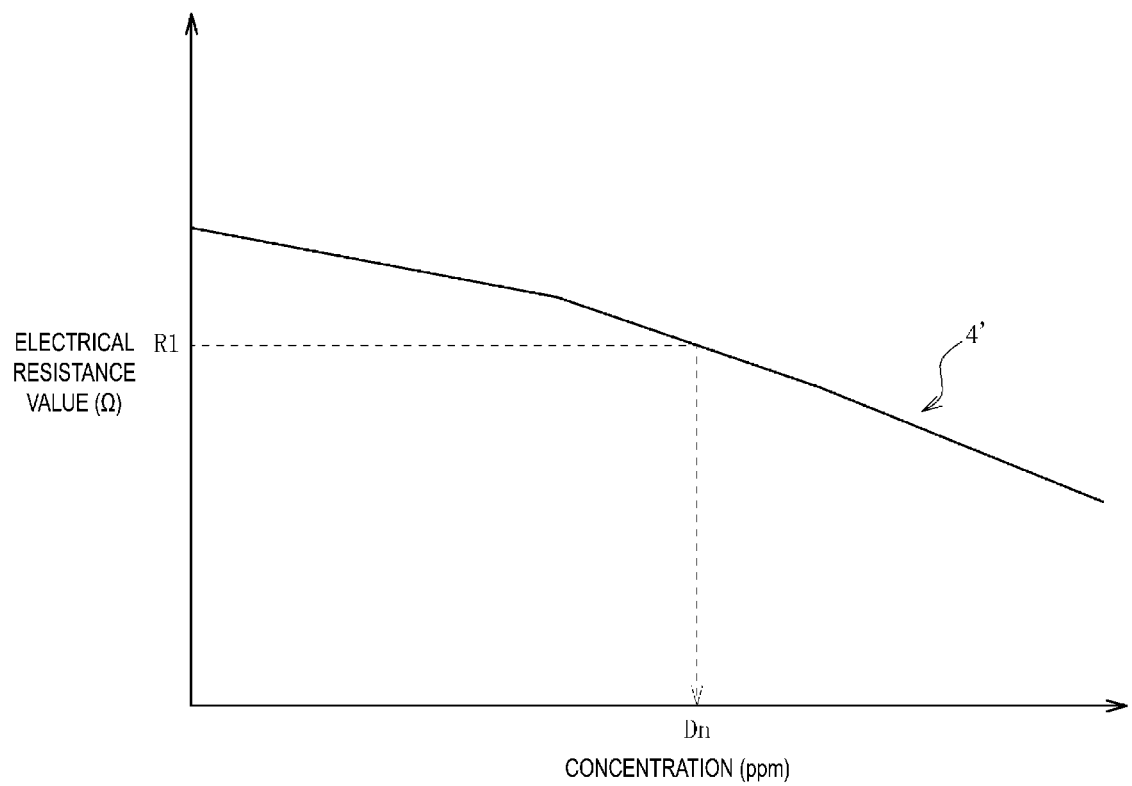
FIG. 11 is a diagram illustrating the method for calculating a concentration of a two component gas in a gas concentration calculating step.

In the gas component concentration calculating step S9, using the calibration curve 4' in the reference sensor element corrected in the calibration curve correcting step S8, a concentration Dn of the two component gas of the hydrogen and the carbon monoxide at an electrical resistance value R1 in the first measuring step S5 is calculated (see FIG. 3 and FIG. 11). The reason why the electrical resistance value R1 in the first measuring step is applied to the calibration curve 4' is that the electrical resistance value R1 is the resistance value when reaction with both of the hydrogen and the carbon monoxide occurs. Additionally, because an electrical resistance value R2 in the second measuring step is a resistance value when only the hydrogen reacts, the application of R2 to the calibration curve 4' is not suitable. In this way, the two component gas concentration Dn of the hydrogen and the carbon monoxide in the reference sensor element 2 can be calculated.

Figure 12:
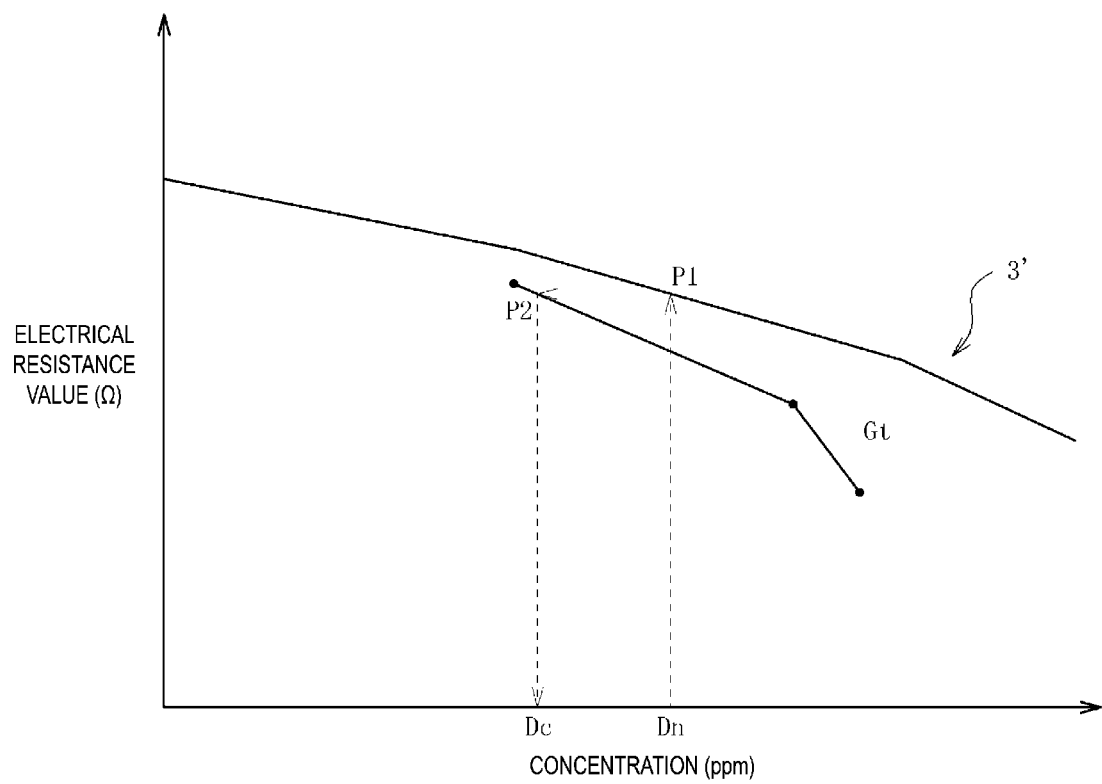
FIG. 12 is a diagram illustrating a method for converting a concentration of the two component gas into a concentration of the detection target gas in a gas component concentration converting step.
Figure 13:
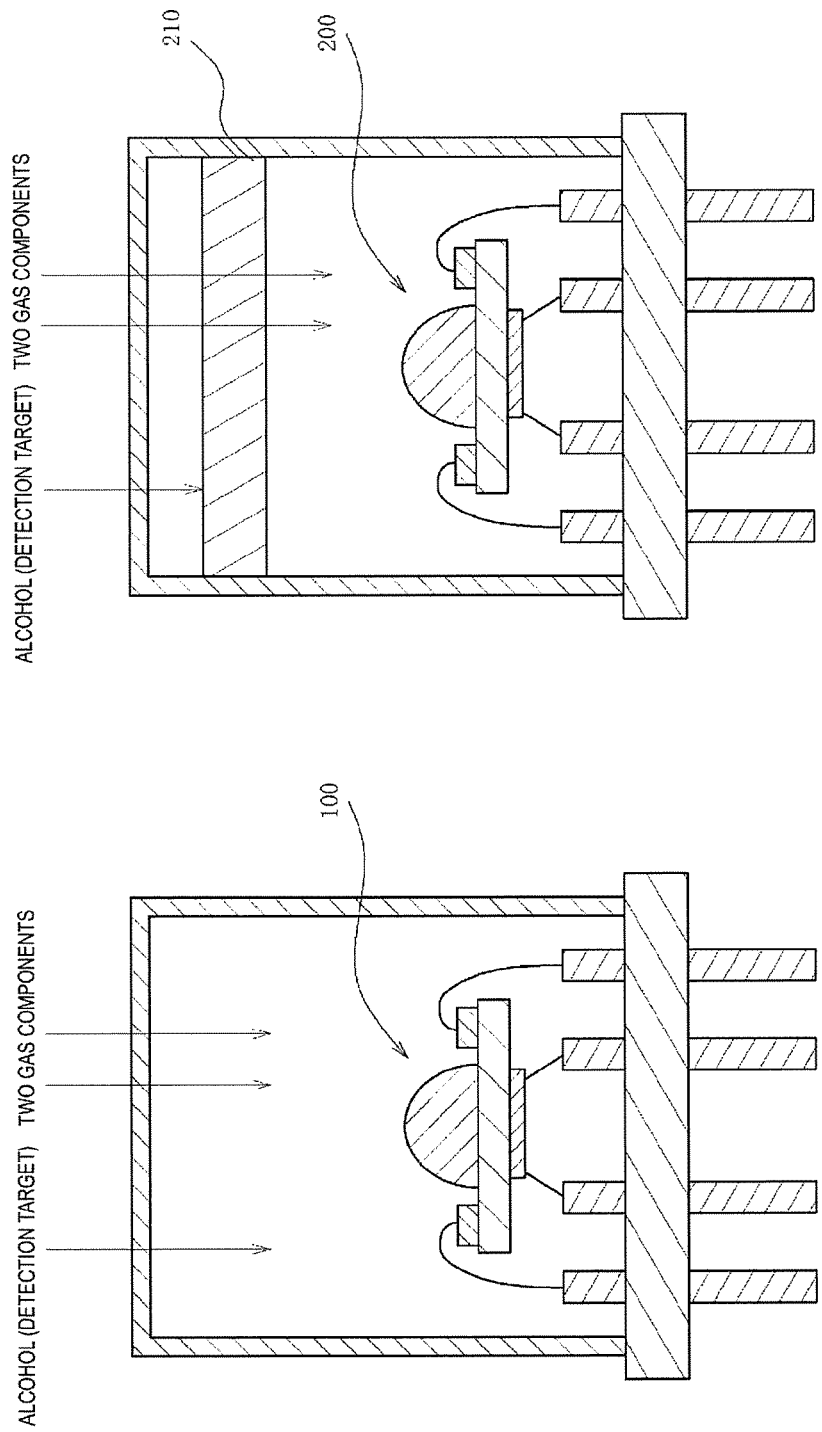
FIG. 13 is a schematic cross-sectional view illustrating a gas sensor device and a reference sensor device used in a conventional detection target gas concentration calculation method.

In the gas component concentration converting step S10, using the calibration curve 3' corrected in the calibration curve correcting step S8, the concentration Dn of the two component gas of the hydrogen and the carbon monoxide calculated in the gas component concentration calculating step S9 is converted into a concentration Dc of the ethanol (see FIG. 12). The calibration curve 3' is the calibration curve of the two component gas of the hydrogen and the carbon monoxide in the gas sensor element 1. The method for converting the concentration is as follows. First, a point P1 where the concentration of the two component gas becomes Dn in the calibration curve 3' is obtained. Next, a point P2 that has the same electrical resistance value as P1 is obtained in the calibration curve of the ethanol. The concentration at P2 becomes the concentration Dc in which the concentration of the two component gas Dn is converted into the ethanol concentration. In other words, the concentration Dc is obtained by converting the concentration of the two component gas in the reference sensor element 2 into the ethanol concentration in the gas sensor element 1.

In the detection target gas concentration calculating step S11, the difference between the interim concentration Dt of the ethanol calculated in the interim concentration calculating step S4 (see FIG. 7) and the concentration Dc of the ethanol (see FIG. 12) calculated in the gas component concentration converting step S10 is calculated. That is, the value calculated by Dt−Dc is the ethanol concentration desired to be obtained finally.

Figure 7:
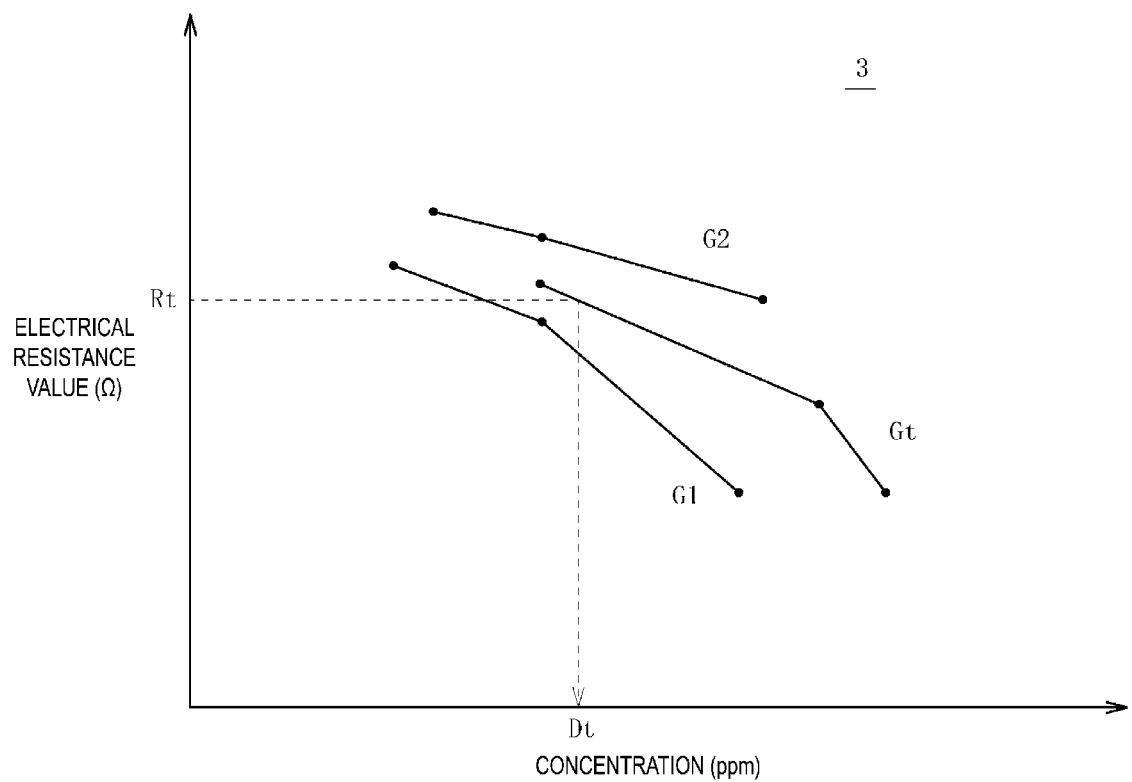
FIG. 7 is a diagram illustrating a method for calculating an interim concentration of a detection target gas in an interim concentration calculating step.
Figure 8:
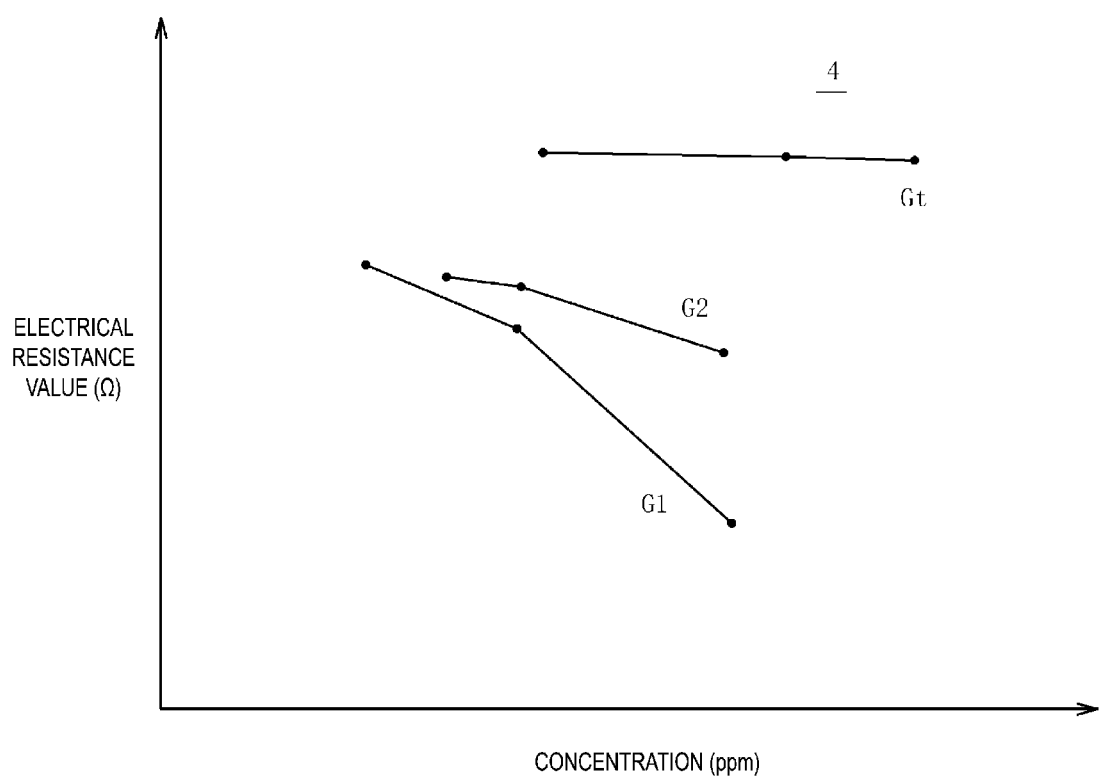
FIG. 8 is a diagram illustrating an example of a calibration curve in the reference sensor element.

Since there is an individual difference in the concentration ratio between the hydrogen and the carbon monoxide in the exhaled gas, it is difficult to preliminarily prepare the calibration curves of the two component gas. Therefore, in the present disclosure, in the reference sensor element 2, the electrical resistance values are measured in the respective first measuring step S5 and second measuring step S6. Then, in the next concentration ratio calculating step S7, the concentration ratio between the hydrogen and the carbon monoxide is calculated from the combination of the two electrical resistance values. Then, in the next calibration curve correcting step S8, the calibration curves in FIG. 7 and FIG. 8 are corrected based on the calculated concentration ratio, and the calibration curves of the two component gas are obtained (see FIG. 9 and FIG. 10). In the next gas component concentration calculating step S9, the concentration of the two component gas in the reference sensor element 2 is calculated using the calibration curve of the two component gas (see FIG. 11). By providing these steps S5 to S9, even when the person exhaling the exhaled gas changes, the concentration ratio of the two component gas in an exhaled gas of a person can be calculated each time, the appropriate calibration curve of the two component gas is obtained, and the exact concentration of the two component gas can be calculated.

Since the calibration curve 4' of the two component gas in the reference sensor element 2 is used for the calculated concentration of the two component gas, the conversion into the ethanol concentration using the calibration curve 3' of the two component gas in the gas sensor element 1 is necessary in the next gas element concentration converting step S10 (see FIG. 12). Finally, the ethanol concentration can be calculated accurately by subtracting the converted ethanol concentration from the interim ethanol concentration.

Note that, in the above description, the interim concentration calculating step S4 is performed concurrently with the first measuring step S5, but may be performed concurrently with any step as long as being performed before the detection target gas concentration calculating step S11.

BRIEF DESCRIPTION OF THE REFERENCE NUMERALS

1: Gas sensor element
2: Reference sensor element
3: Calibration curve in gas sensor element
3': Calibration curve in corrected gas sensor element
4: Calibration curve in reference sensor element
4': Calibration curve in corrected reference sensor element
5: Cover
6: Base
7a, 7b, 7c: Terminal
8a, 8b, 8c: Lead wire
9: Gas introduction hole
10: Wire mesh
11: Gas sensitive body
12: Combined heater-electrode
13: Linear electrode
14: Filter
100: Gas sensor element
200: Reference sensor element
210: Alcohol

The invention claimed is:

1. A method for calculating concentration of detection target gas comprising:
   (a) introducing a detected gas containing two gas components and one detection target gas in a gas sensor element and calculating an interim concentration of the detection target gas;
   (b) introducing the two gas components in a reference sensor element having a same property as a property of the gas sensor element, heating the reference sensor element to a temperature at which both of the two gas components react, and maintaining the temperature for a predetermined period to measure an electrical resistance value of the reference sensor element concurrently with (a), wherein the gas sensor element and the reference sensor element are metal oxide based gas sensor elements;
   (c) heating the reference sensor element to a temperature at which only one of the two gas components reacts, and maintaining the temperature for a predetermined period to measure an electrical resistance value of the reference sensor element;
   (d) calculating a concentration ratio of the two gas components based on a combination of the electrical resistance value in (b) and the electrical resistance value in (c);
   (e) correcting a calibration curve of the two gas components in the gas sensor element and a calibration curve of the two gas components in the reference sensor element preliminarily prepared based on the concentration ratio;
   (f) using the calibration curve in the reference sensor element corrected in (e) to calculate a concentration of the two gas components at the electrical resistance value in (b);
   (g) using the calibration curve in the gas sensor element corrected in (e) to convert the concentration of the two gas components calculated in (f) into a concentration of the detection target gas; and
   (h) calculating a difference between the interim concentration of the detection target gas calculated in (a) and the concentration of the detection target gas converted in (g).

2. The method for calculating concentration of detection target gas according to claim 1, wherein
   the detected gas is an exhaled gas, the two gas components are hydrogen and carbon monoxide, and the detection target gas is ethanol.

* * * * *